United States Patent [19]

Wittrock et al.

[11] Patent Number: 5,482,067

[45] Date of Patent: Jan. 9, 1996

[54] INSTRUMENT CLEANING CASSETTE WITH GUIDED DOUBLE HINGE

[76] Inventors: Paul Wittrock; Paul Porteous; Don D. Porteous, all of 600 E. Hueneme Rd., Oxnard, Calif. 93033

[21] Appl. No.: 388,012

[22] Filed: Feb. 15, 1995

[51] Int. Cl.[6] .................................................. B08B 3/10
[52] U.S. Cl. ...................... 134/135; 134/184; 134/115 R; 134/201; 206/363; 206/207
[58] Field of Search .................................... 206/207, 363, 206/364, 365, 366, 368, 369; 422/294, 297, 300; 134/1, 184, 186, 200, 115, 135, 201; 68/355; 366/127

[56] References Cited

U.S. PATENT DOCUMENTS

| | | | |
|---|---|---|---|
| 2,702,260 | 2/1955 | Massa | 134/184 |
| 2,985,003 | 5/1961 | Gelfand et al. | 134/184 |
| 2,994,332 | 8/1961 | Leonhardt | 134/184 |
| 3,034,520 | 5/1962 | Jewell | 366/127 |
| 3,638,666 | 2/1972 | Fishman | 134/184 |
| 3,640,295 | 2/1972 | Peterson | 134/184 X |

FOREIGN PATENT DOCUMENTS 2547554  4/1977  Germany ............................... 134/184

*Primary Examiner*—Frankie L. Stinson
*Attorney, Agent, or Firm*—Louis J. Bachand

[57] ABSTRACT

A cassette for retaining medical, dental and veterinary instruments during fluid-carried ultrasonic vibration cleaning comprising generally rectangular, registered top and bottom interiorly open solid frames formed of synthetic organic plastic material having a tendency to dampen ultrasonic vibrations and molded to define interior instrument supports and resistant to cleaning conditions and defining a recess sized to receive the instruments, a series of separately formed and movable instrument support brackets, a series of support bracket mounts within the cavity integrally formed with the frames in opposed registration for mounting the support brackets in instrument receiving relation; a hinge linking like ends of the top and bottom frames for hinged pivoted movement opening and closing the cassette to receive and disgorge the instruments, the hinge comprising on each of the top and bottom frames a hinge pin and flange arrangement and an elongated link having an intermediate extent and terminal portions journaling the hinge pins for separate hinging movement such that the frames are registerable with each other in normal position to form the cavity and in inverted position to provide a display of the instruments in one frame elevated by being atop the other frame inverted and registered, and separately formed fluid-passing top and bottom frame panels respectively closing the top and bottom frames to contain the instruments within the cassette against injury to persons handling the cassette, the top and bottom frame panels being metallic and fluid porous to have less tendency to dampen ultrasonic vibrations than the frames, the cassette being molded to receive the instruments and the instruments being cleanable within the cassette by ultrasonic means.

25 Claims, 3 Drawing Sheets

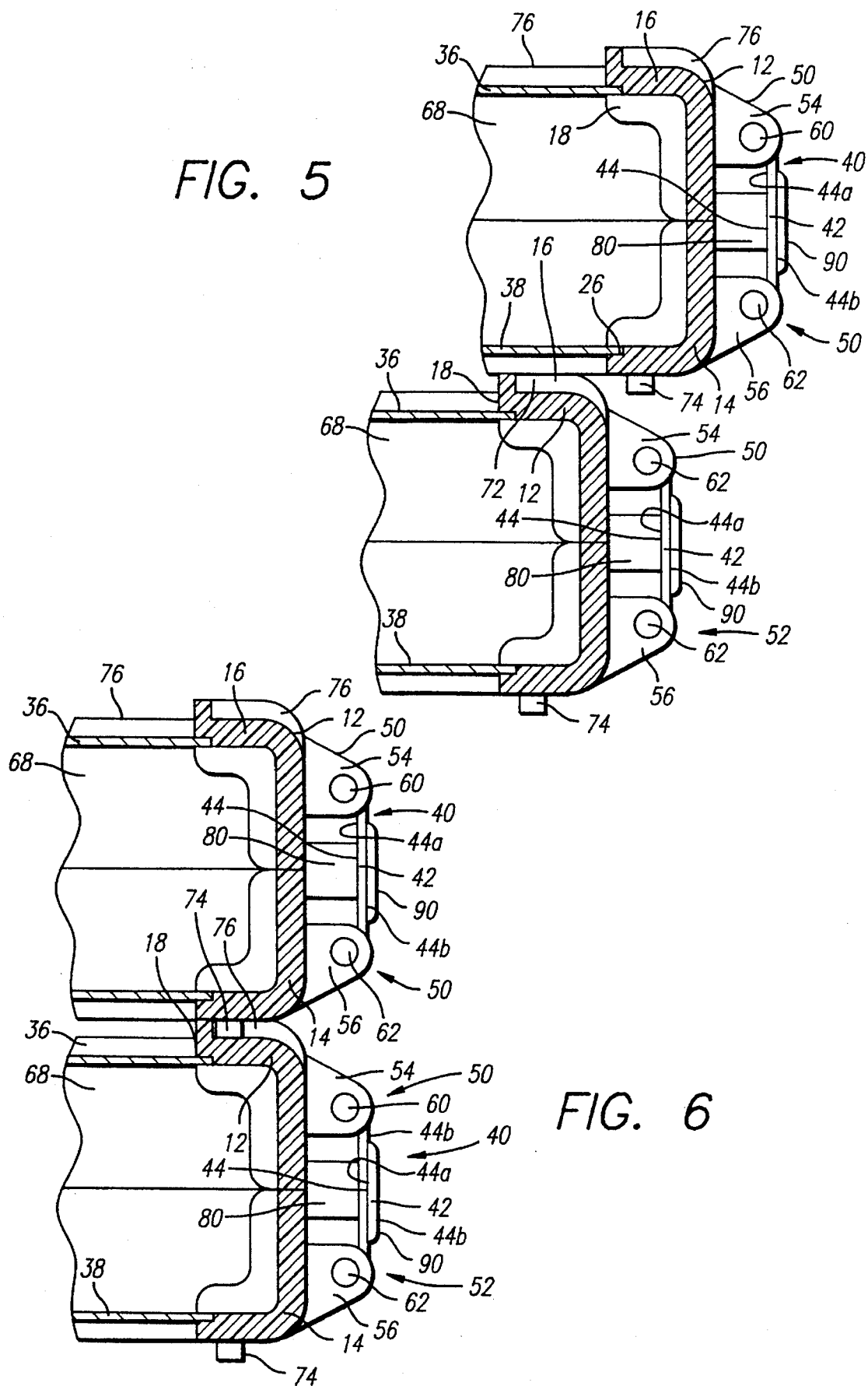

INSTRUMENT CLEANING CASSETTE WITH GUIDED DOUBLE HINGE

TECHNICAL FIELD

This application relates to medical, dental and veterinary instrument cleaning and more particularly to improved means for effecting such cleaning. In a particular aspect the invention provides an instrument cleaning cassette which has all the convenience of molded plastic in terms of ideal shape, easy molding to desired configuration, low manufacturing cost, low weight, and care-free handling and simultaneously delivers the faithful ultrasonic vibration transmission of all-metal cassettes without the vibration damping typically associated with plastics, and without the limited design freedom, excessive weight, and high cost of manufacture identified with all-metal cassettes. Further, the invention cassette avoids excessive condensation problems following sterilization procedures.

BACKGROUND OF THE INVENTION

Cassettes typically hold a variety of instruments for cleaning of gross residues by immersion in a bath through which ultrasonic energy is passed in a liquid vehicle. The instruments are subsequently sterilized in a separate procedure frequently involving autoclave steam sterilization. Transmission of the vibrations into contact with the instruments is essential to effective cleaning. Improvements in instrument cleaning cassettes to lower cost, improve handling and durability are desirable but such improvements should not come at the cost of lessened cleaning effectiveness. Nor should excessive condensate after steam sterilization be endured. Metal cassettes are heavy and awkward to handle and typically have sharp edges which can readily tear enclosure pouches, generally formed of plastic and cellulosic films, in which the cassettes and their contents are sterilized and stored for use. Failure of the cassette to dissipate sterilization steam without excessive condensation can cause moisture damage to the pouch and allow breach of sterile conditions in the pouch through wicking where excessive water is present.

SUMMARY OF THE INVENTION

It is accordingly an object of the invention to provide an improved cleaning cassette. It is a further object to provide a cleaning cassette in which the easy moldability and design freedom, as well as lightness of weight and comfortable handling of plastic material in the cassette frame is combined with the ultrasonic vibration transmissibility of metal in the frame panels so that the loss of vibration transmissibility from use of the plastic is minimized and effective cleaning is readily accomplished while adding the benefits of plastic material use. A still further object is to provide such a cassette in which the frames lie in registered position whether opened in an instrument display mode or closed in a cleaning mode, and in which the transition between the open or closed mode is effected without misalignment of the frames through hinge action. Yet another object is to provide a cleaning cassette in which the aligned frames lock in position when opened in the display mode and also when stacked with similar cassette in vertical array. A still further object is to provide a cassette of plastic material to be flee of pouch-damaging sharp edges and metal as well to be flee of excessive condensation leading to damage to the pouch.

These and other objects of the invention to become apparent hereinafter are realized in a cleaning cassette for retaining medical, dental and veterinary instruments during fluid-carried ultrasonic vibration cleaning, the cassette being normally horizontally disposed for loading and unloading and comprising registered top and bottom open frames formed of synthetic organic plastic material resistant to cleaning conditions and having a tendency to dampen ultrasonic vibration, the frames being molded to a size and configuration for receiving and holding the instruments, the top and bottom frames being relatively movable for opening the cassette to receive the instruments, and separately formed top and bottom frame panels respectively closing the top and bottom frames to contain the instruments within the cassette against injury to persons handling the cassette, the top and bottom frame panels being metallic and having less tendency to dampen ultrasonic vibrations than the frames, whereby the cassette frame is inexpensively moldable in an instrument-receiving configuration and the instruments are cleanable within the cassette by ultrasonic means.

In this and like embodiments, the top or bottom frame panel is generally apertured to have fluid-passing porosity to fluid carrying ultrasonic vibrations, or both the top and bottom frame panels are generally apertured to have fluid-passing porosity to fluid carrying ultrasonic vibrations, there is a hinge connecting the top and bottom frames, the top and bottom frames define outwardly facing, cooperating locking structure adapted to maintain a plurality of the cassettes in vertically stacked relation, and there is also included a plurality of bottom frames of different depths each separately registerable with the top frame in cassette capacity varying relation.

In a more preferred form of the invention there is provided a cleaning cassette for retaining medical, dental and veterinary instruments during fluid-carried ultrasonic vibration cleaning, the cassette being normally horizontally disposed for loading and unloading and comprising generally rectangular, registered, top and bottom interiorly open solid frames formed of synthetic organic plastic material resistant to cleaning conditions and having a tendency to dampen ultrasonic vibration, the frames defining a recess sized to receive the instruments, a hinge linking the top and bottom frames for hinged movement opening and closing the cassette to receive and disgorge the instruments, and separately formed fluid-passing top and bottom frame panels respectively closing the top and bottom frames to contain the instruments within the cassette against injury to persons handling the cassette, the top and bottom frame panels being metallic and fluid-porous to have less tendency to dampen ultrasonic vibrations than the frames, whereby the instruments are cleanable within the cassette by ultrasonic means.

In this and like embodiments, typically, the hinge comprises an elongated link having an intermediate extent and terminals at opposite ends thereof pivoted respectively on the top and bottom frames such that the frames register with each other in normal face to face or inverted back to back position, the hinge further comprises opposed pairs of hinge brackets defined by the top and bottom frames, and a pair of hinge pins each supported by a pair of the hinge brackets, the terminals journaling the hinge pins in top and bottom frame hinging relation, the link is separately formed from the bracket pairs, the hinge is a first hinge and there is also included a second hinge like the first hinge and laterally adjacent thereto on the frame ends, there is also included cooperating fastener structure on the top and bottom frames at the frame ends opposite the hinge, each top and bottom frame comprises wall having an internal flange defining the frame recess, the frame panels being supported on the internal flanges in opposed, cassette cavity defining relation, there is also included means blocking misaligning relative movement of the top and bottom frames when pivoting on the hinge, which blocking means comprises an inward facing boss on the hinge link intermediate extent arranged to block a pivoting top or bottom frame from such close approach to the hinge link intermediate portion that the pivoting frame will not register with its opposing frame when fully rotated to the opposing frame, each top and bottom frame comprises a wall having an internal flange defining the frame recess, the hinge boss engaging a top or bottom frame wall in spaced relation to the hinge link intermediate portion upon relative movement of the top and bottom frames, whereby the frames are guided away from the hinge intermediate portion and into registration with each other, at least one of the top and bottom frame panels is laterally and longitudinally perforated for passing fluid carrying ultrasonic vibrations, there is also included instrument support brackets within the cassette cavity, the frames defining within the cavity a series of bracket mounts for maintaining the support brackets in instruments mounting position, the top and bottom frames define outward facing, cooperating locking structure to maintain a plurality of the cassettes in vertically stacked relation, the blocking means includes a second blocking means comprising an outward facing boss on said hinge link intermediate extent arranged to block a top or bottom frame being pivoted into back to back relation with its opposed frame from such close approach to the hinge link intermediate portion that said pivoting frame will not register with opposing frame when fully rotated, and there is further included a plurality of bottom frames each comprising a wall, the walls having inward flanges arranged to support a bottom frame panel at different depths relative to the top wall panel, each bottom frame being separately registerable with the top frame in cassette capacity varying relation.

In a highly particular embodiment there is provided a cleaning cassette for retaining medical, dental and veterinary instruments during fluid-carded ultrasonic vibration cleaning, the cassette being normally horizontally disposed for loading and unloading and comprising generally rectangular, registered top and bottom interiorly open solid frames formed of synthetic organic plastic material molded to define interior instrument supports and resistant to cleaning conditions, the frames having a tendency to dampen ultrasonic vibration, each of the frames defining a recess sized to receive the instruments, a series of separately formed and movable instrument support brackets, a series of support bracket mounts within the cavity integrally formed with the frames in opposed registration for mounting the support brackets in instrument receiving relation; a hinge linking like ends of the top and bottom frames for hinged pivoted movement opening and closing the cassette to receive and disgorge the instruments, the hinge comprising on each of the top and bottom frames a hinge pin and flange arrangement and between the hinge pins an elongated link having an intermediate extent and terminal portions journaling the hinge pins for separate hinging movement such that the frames are registerable with each other in normal face to face position to form the cavity and in inverted back to back position to provide a display of the instruments in one frame elevated by being atop the other frame inverted and registered, and separately formed fluid-passing top and bottom frame panels respectively closing the top and bottom frames to contain the instruments within the cassette against injury to persons handling the cassette, the top and bottom frame panels being metallic and fluid-porous to have less tendency to dampen ultrasonic vibrations than the frames, whereby the cassette is molded to receive the instruments and the instruments are cleanable within the cassette by ultrasonic means.

In this just-mentioned embodiment, typically the frames define at their corners cooperating interlocking structure for holding the frames of a single cassette in locked relation when back-to-back in inverted relation, and holding the frames of vertically successive cassettes in locked relation when the frames are face-to-face in cassette cavity defining relation, the hinge elongated link defines structure to engage one said frames in rotation toward the other of said frames to align said frames in registration in face to face or back to back relation, and said hinge link blocking structure includes both an inward facing boss which is arranged to engage said frames in frame shitting relation so that said frames are in face to face registration when closed to define said cassette cavity, and an outward facing boss which is arranged to engage said frames in frame shifting relation so that said frames are in back to back registered relation when opened.

BRIEF DESCRIPTION OF THE DRAWINGS

The invention will be further described in conjunction with the attached drawings in which:

FIG. 5 is a view of two cassette in stacked offset relation; and,

FIG. 6 is a view of two cassettes in stacked registered relation.

DESCRIPTION OF THE PREFERRED EMBODIMENTS

Figure 1:
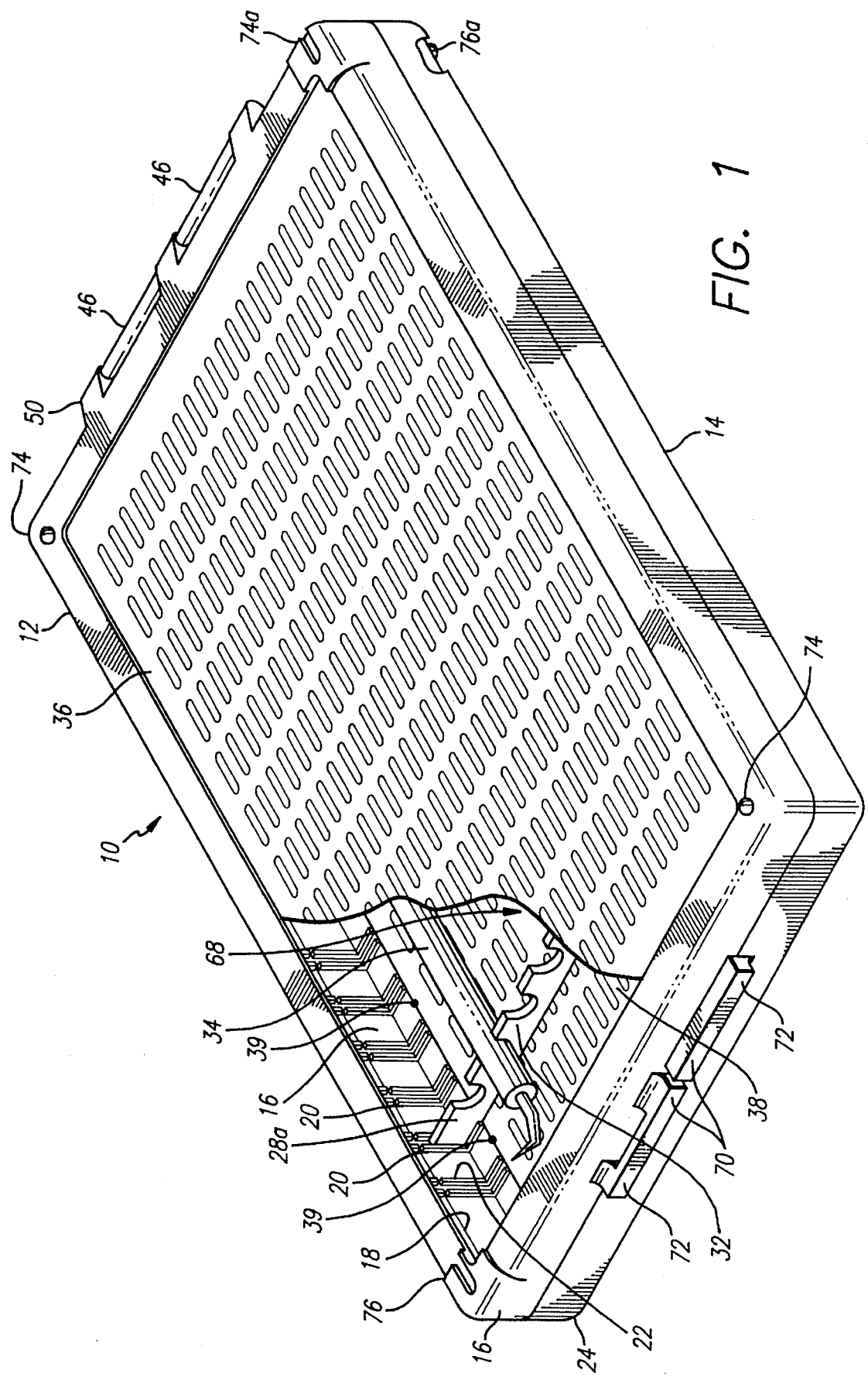
FIG. 1 is an isometric view of the invention cleaning cassette.

With reference now to the drawings in detail, in FIG. 1, the invention cleaning cassette is shown at 10 comprising a synthetic organic plastic top frame 12 and bottom frame 14. The frames 12 and 14 can be injection molded or otherwise formed from any of the rigid moldable synthetic organic plastics available in the trade having resistance to ultrasonic cleaning conditions. Top frame 12 is generally rectangular and comprises a wall 16 having at its upper extent flange 18 extending inwardly. A series of support bracket mounts 20 comprising slots 22 are formed about the inner periphery of the top frame wall 16 and extending onto the flange 18. Bottom frame 14 is congruent with top frame 12, comprises a wall 24 having at it lower extent flange 26 extending inwardly. A series of support bracket mounts 28 comprising slots 30 are formed about the inner periphery of the bottom frame wall 24 and extending onto the flange 26.

Support bracket 32 is positioned transversely of the cassette 10 secured in bracket support mounts, e.g. mount 28a. Medical, dental or veterinary instrument 34 is then supported by bracket 32 is stable position for carriage with the cassette, for cleaning while in the cassette, or for display for use by turning the top frame 12 under the bottom frame 14 as a pedestal.

Most plastics useful for molding a product such as the invention cassette tend to dampen ultrasonic vibration being transmitted through a fluid medium, and thus use of plastics in these applications has been counter indicated and the many benefits of plastics lost to the cleaning cassette. These plastics as well appear to not dissipate autoclave steam engendered moisture in the sterilization pouch following sterilization operations such that moisture, particularly on the cellulosic portion of the pouches, is present to the degree that wicking can occur across the cellulosic barrier contaminating the sterilized zone. It has been observed that such excessive, nondissipated moisture is not prevalent in sterilization of metal cassettes. The present cassette 10 has sufficient metal to adequately dissipate moisture whereas a wholly plastic cassette will not. On the other hand, the present cassette 10 has plastic adequate to reduce weight and configured to avoid the sharp edges inevitably found in metal cassettes.

In the present invention, moreover, the vibration damping properties of plastics are not a problem because the invention cleaning cassette uses metal panels 36, 38 secured in top frame 12 and bottom frame 14 as by interfitment with fastening pins 39 molded into the frames. It has been found that such panels 36, 38, when suitably perforate, enable effective ultrasonic vibration cleaning of instruments 34 within the cassette. The panel 36, 38 perforations can be stamped in a thin metal sheet, or be resultant from use of screen material or webbing in forming the panel arranged to provide fluid passing openings and to guard against protrusion from or hand accessibility to the instruments within the closed cassette. Panels 36, 38 are enclosed by the top and bottom frames 12, 14 so that the handling disadvantages of metal are avoided and the panels are themselves relatively small such that weight increase is not a problem. Thus the advantages of plastic noted herein are realized while maintaining the vibration transmission capabilities of metal in the cassette 10. The metal panels 36, 38 are perforated so as to transmit the fluid carried ultrasonic vibrations while at the same time covering the cassette-enclosed instruments against accidental contact with persons handling the cassette.

The cassette 10 is further advantageous is providing a pedestal for display of the sterilized instruments for use. The top frame 12 folds under bottom frame 14 as noted. In order for the frames 12, 14 to fold thusly, the frames are joined by a double hinge 40 best shown in FIGS. 2–4. The hinge 40 comprises a link 42 having an intermediate extent 44 and opposite terminals 46, 48. The top and bottom frames 12, 14 are provided with hinge brackets 50, 52 defined by projecting ears 54, 56 on the smaller dimension of top and bottom frame walls 16, 24. Hinge pins 60, 62 are fixed in the hinge brackets 50, 52. Link terminals 46, 48 define hinge pin journals 64, 66. Because the hinge 40 is doubly pivoted as shown the top and bottom frames 12, 14 can be registered with one another with the frames defining a cavity 68 (FIG. 1) or with the frames oppositely facing, e.g. the top frame 12 is under bottom frame 14 and forms the mentioned pedestal.

As an aid to maintaining registration of the top and bottom frames 12, 14 when in cavity defining relation a latch means 70 is provided comprising detenting tabs 72 which snap over the opposite wall 16, 24 when the frames are thus aligned.

Figure 2:
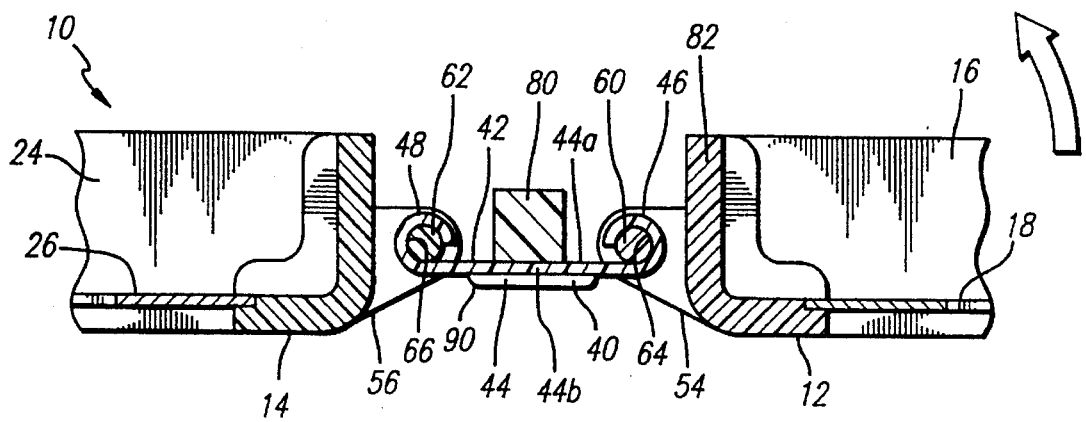
FIG. 2 is a detail view, enlarged, of the cassette hinge opened, in advance of inverting the right hand top frame below the left hand bottom frame.
Figure 3:
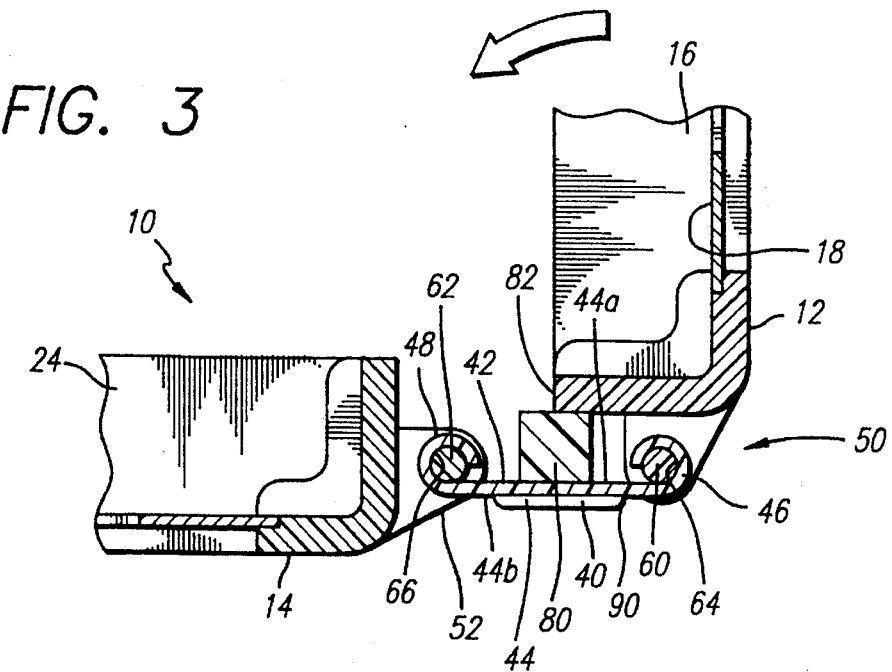
FIG. 3 is a view of the hinge in transition from open to closed.
Figure 4:
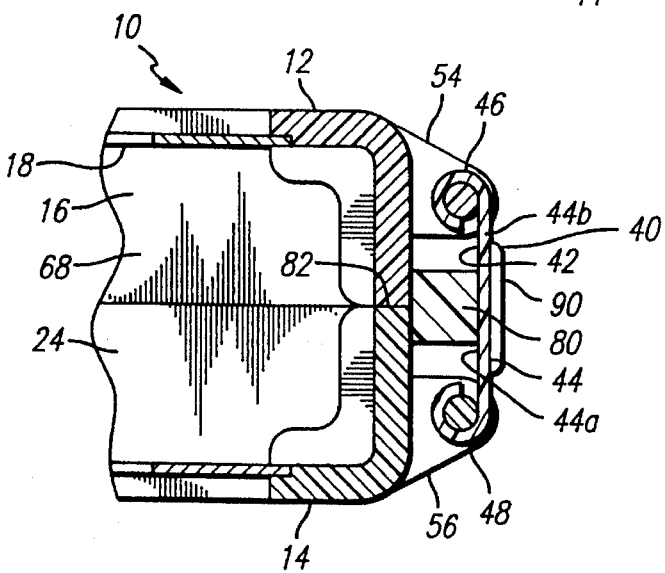
FIG. 4 is a view of the hinge in closed condition.

Hinge 40 will permit the frames 12, 14 it shift longitudinally and this shift can result in misalignment of the frames and failure to be latchable. To avoid this inconvenience in use, the invention includes provision for blocking misalignment even as the frames 12, 14 are pivoted one toward the other. With particular reference to FIGS. 2–4, an inward facing boss 80 is shown on link 42, positioned along the inner face 44a of link intermediate extent 44 so as to engage the edge 82 of the top frame wall 16 as the frame 12 moves toward frame 14. This engagement prevents the wall edge 82 from so far approaching the link 42 that the frames 12, 14 can become misaligned and fail to register. The boss 80 guides the frame 12 along the proper course to perfect alignment, as shown.

Proper alignment of the frames 12, 14 when in the display mode, one frame inverted on the other, back to back, is ensured by providing an outward facing boss 90 on the back of intermediate link 42 positioned on the outer face 44b of the intermediate link. The boss 90 functions in the manner of boss 80 in that the frame 12 or 14 being pivoted back around the hinge 40 engages the boss 90 and is shifted thereby from coming so close to the other frame that misalignment and nonregistration of the back to back frames occurs.

Boss 80 and boss 90 is formed as a local enlargement of the intermediate link 44 as shown, or as a protuberance integrally formed with the link, or added on as a separate element with a thickness in the case of the boss 80 such that the boss fills the gap between the intermediate link 42 and the outer surface of the frames 12, 14, and in the case of the boss 90 a thickness such that the frames are engaged and shifted into registration when pivoting on the hinge 40 and into a back to back position.

With particular reference to FIGS. 1, 5 and 6, as an aid to maintaining registration of the top and bottom frames 12, 14 when in pedestal arrangement, a pin and slot fastener system is provided including pins 74 and slots 76 arranged on alternating corners of the frames, facing outward (upward) and cooperative to interlock the frames. The alternation of pins and slots 74, 76 is true vertically as well as horizontally so that for example below slot 76a formed in top frame 12 in FIG. 1 there is a pin 74a formed in bottom frame 14. This alternation of pins and slots, or of other cooperating fastener arrangement, enables securement of vertically successive cassettes in a stack, as in a bath or sterilization cabinet without fear of the cassettes falling into positions of random repose, See FIG. 6.

The invention thus provides an improved cleaning cassette in which the easy moldability and design freedom, as well as lightness of weight and comfortable handling of plastic material in the cassette frame is combined with the ultrasonic vibration transmissibility of metal in the frame panels so that the loss of vibration transmissibility from use of the plastic is minimized and effective cleaning is readily accomplished while adding the benefits of plastic material use. Further the cassette frames lie in registered position whether opened in an instrument display mode or closed in a cleaning mode, and transition between the open, display, or closed mode is effected without misalignment of the frames through hinge action, and the aligned cassette frames lock in position when opened in the display mode and also when stacked with similar cassette in vertical array. The foregoing objects of the invention are thus met.

We claim:

1. Cassette for retaining medical, dental and veterinary instruments during fluid-carried ultrasonic vibration cleaning, said cassette being normally horizontally disposed for loading and unloading and comprising registered top and bottom open frames formed of synthetic organic plastic material resistant to cleaning conditions and having a tendency to dampen ultrasonic vibration, said frames being molded to a size and configuration for receiving and holding said instruments, said top and bottom frames being relatively movable for opening said cassette to receive said instruments, and separately formed top and bottom frame panels respectively closing said top and bottom frames to contain said instruments within said cassette against injury to persons handling said cassette, said top and bottom frame panels being metallic and having less tendency to dampen ultrasonic vibrations than said frames, whereby said cassette frame is inexpensively moldable in an instrument-receiving configuration and said instruments are cleanable within said cassette by ultrasonic means.

2. Cassette according to claim 1, in which said top or bottom frame panel is generally apertured to have fluid-passing porosity to fluid carrying ultrasonic vibrations.

3. Cassette according to claim 1, in which said top and bottom frame panels are generally apertured to have fluid-passing porosity to fluid carrying ultrasonic vibrations.

4. Cassette according to claim 1, including also a hinge connecting said top and bottom frames.

5. Cassette according to claim 4, including also a plurality of bottom frames of different depths each separately registerable with said top frame in cassette capacity varying relation.

6. Cassette according to claim 1, in which said top and bottom frames define outwardly facing, cooperating locking structure adapted to maintain a plurality of said cassettes in vertically stacked relation.

7. Cassette for retaining medical, dental and veterinary instruments during fluid-carried ultrasonic vibration cleaning, said cassette being normally horizontally disposed for loading and unloading and comprising generally rectangular, registered, top and bottom interiorly open solid frames formed of synthetic organic plastic material resistant to ultrasonic cleaning conditions and having a tendency to dampen ultrasonic vibration, said frames defining a recess sized to receive said instruments, a hinge linking said top and bottom frames for hinged movement opening and closing said cassette to receive and disgorge said instruments, and separately formed fluid-passing top and bottom frame panels respectively closing said top and bottom frames to contain said instruments within said cassette against injury to persons handling said cassette, said top and bottom frame panels being metallic and fluid-porous to have less tendency to dampen ultrasonic vibrations than said frames, whereby said instruments are cleanable within said cassette by ultrasonic means.

8. Cassette according to claim 7, in which said hinge comprises an elongated link having an intermediate extent and terminals at opposite ends thereof pivoted respectively on said top and bottom frames such that said frames register with each other in face to face or back to back position.

9. Cassette according to claim 8, in which said hinge further comprises opposed pairs of hinge brackets defined by said top and bottom frames, and a pair of hinge pins each supported by a pair of said hinge brackets, said terminals journaling said hinge pins in top and bottom frame hinging relation.

10. Cassette according to claim 9, in which said link is separately formed from said bracket pairs.

11. Cassette according to claim 9, in which said hinge is a first hinge and including also a second hinge like said first hinge and laterally adjacent thereto on said frame ends.

12. Cassette according to claim 8, including also cooperating fastener structure on said top and bottom frames at the frame ends opposite said hinge.

13. Cassette according to claim 8, in which each said top and bottom frame comprises wall having an internal flange defining said frame recess, said frame panels being supported on said internal flanges in opposed, cassette-cavity defining relation.

14. Cassette according to claim 8, including also means blocking misaligning relative movement of said top and bottom frames when pivoting on said hinge.

15. Cassette according to claim 14, in which said blocking means includes a first blocking means comprising an inward facing boss on said hinge link intermediate extent arranged to block a top or bottom frame being pivoted into face to face relation with its opposing frame from such close approach to said hinge link intermediate portion that said pivoting frame will not register with its opposing frame when fully rotated to said opposing frame.

16. Cassette according to claim 15, in which each said top and bottom frame comprises a wall having an internal flange defining said frame recess, said hinge boss engaging a top or bottom frame wall in spaced relation to said hinge link intermediate portion upon relative movement of said top and bottom frames, whereby said frames are guided away from said hinge intermediate portion and into registration with each other.

17. Cassette according to claim 16, in which at least one of said top and bottom frame panels are laterally and longitudinally perforated for passing fluid carrying ultrasonic vibrations.

18. Cassette according to claim 17, including also instrument support brackets within said cassette cavity, said frames defining within said cavity a series of bracket mounts for maintaining said support brackets in instruments mounting position.

19. Cassette according to claim 18, in which said top and bottom frames define outward facing, cooperating locking structure to maintain a plurality of said cassettes in vertically stacked relation.

20. Cassette according to claim 19, including also a plurality of bottom frames each comprising a wall, said walls having inward flanges arranged to support a bottom frame panel at different depths relative to said top wall panel, each bottom frame being separately registerable with said top frame in cassette capacity varying relation.

21. Cassette according to claim 15, in which said blocking means includes a second blocking means comprising an outward facing boss on said hinge link intermediate extent arranged to block a top or bottom frame being pivoted into back to back relation with its opposed frame from such close approach to said hinge link intermediate portion that said pivoting frame will not register with its opposing frame when fully rotated onto said opposing frame.

22. Cassette for retaining medical, dental and veterinary instruments during fluid-carried ultrasonic vibration cleaning, said cassette being normally horizontally disposed for loading and unloading and comprising generally rectangular, registered top and bottom interiorly open solid frames formed of synthetic organic plastic material molded to define interior instrument supports and resistant to cleaning conditions, said frames having a tendency to dampen ultrasonic vibration, each of said frames defining a recess sized to receive said instruments, a series of separately formed and movable instrument support brackets, a series of support bracket mounts within said cavity integrally formed with said frames in opposed registration for mounting said support brackets in instrument receiving relation; a hinge linking like ends of said top and bottom frames for hinged pivoted movement opening and closing said cassette to receive and disgorge said instruments, said hinge comprising on each of said top and bottom frames a hinge pin and flange arrangement and between said hinge pins an elongated link having an intermediate extent and terminal portions journaling said hinge pins for separate hinging movement such that said frames are registerable with each other in normal position to form said cavity and in inverted position to provide a display of said instruments in one frame elevated by being atop the other frame inverted and registered, and separately formed fluid-passing top and bottom frame panels respectively closing said top and bottom frames to contain said instruments within said cassette against injury to persons handling said cassette, said top and bottom frame panels being metallic and fluid-porous to have less tendency to dampen ultrasonic vibrations than said frames, whereby said cassette is molded to receive said instruments and said instruments are cleanable within said cassette by ultrasonic means.

23. Cassette according to claim 22, in which said frames define at their corners cooperating interlocking structure for holding the frames of a single cassette in locked relation when back-to-back in inverted relation, and holding the frames of vertically successive cassettes in locked relation when said frames are face-to-face in cassette cavity defining relation.

24. Cassette according to claim 23, in which said hinge link blocking structure includes an inward facing boss which is arranged to engage said frames in frame shifting relation so that said frames are in face to face registration when closed to define said cassette cavity, and an outward facing boss which is arranged to engage said frames in frame shifting relation so that said frames are in back to back registered relation when opened.

25. Cassette according to claim 22, in which said hinge elongated link defines structure to block engage one or another said frames in rotation toward the other of said frames to align said frames in registration in face to face or back to back relation.

* * * * *